(12) United States Patent
She et al.

(10) Patent No.: US 10,842,715 B2
(45) Date of Patent: Nov. 24, 2020

(54) INFUSION ACCESSORY CAPABLE OF DETECTING INFUSION LIQUID PARAMETERS AND METHOD OF DETECTING INFUSION LIQUID PARAMETERS

(71) Applicant: Zhaowei She, Guangdong (CN)

(72) Inventors: Zhaowei She, Guangdong (CN); Jie Zhao, Beijing (CN); Limin She, Guangdong (CN)

(73) Assignee: Zhaowei She, Foshan (CN)

( * ) Notice: Subject to any disclaimer, the term of this patent is extended or adjusted under 35 U.S.C. 154(b) by 540 days.

(21) Appl. No.: 15/749,121

(22) PCT Filed: Jul. 22, 2016

(86) PCT No.: PCT/CN2016/090957
§ 371 (c)(1),
(2) Date: Jan. 31, 2018

(87) PCT Pub. No.: WO2017/020731
PCT Pub. Date: Feb. 9, 2017

(65) Prior Publication Data
US 2018/0214344 A1 Aug. 2, 2018

(30) Foreign Application Priority Data
Jul. 31, 2015 (CN) .......................... 2015 1 0470769

(51) Int. Cl.
A61J 1/18 (2006.01)
A61J 1/20 (2006.01)
(Continued)

(52) U.S. Cl.
CPC .............. A61J 1/18 (2013.01); A61J 1/2037 (2015.05); A61J 1/2051 (2015.05);
(Continued)

(58) Field of Classification Search
CPC .......... A61J 1/18; A61J 1/2037; A61J 1/2051; A61J 1/065; A61J 2200/70; A61M 5/16854; A61M 29/24; G01N 33/15
(Continued)

(56) References Cited

U.S. PATENT DOCUMENTS 8,584,539 B2 * 11/2013 Wright ................... G01N 33/15
73/866
9,452,255 B2 * 9/2016 Tieck .................. A61M 5/1413
(Continued)

FOREIGN PATENT DOCUMENTS

CN 1615165 A 5/2005
CN 101852689 A 10/2010
(Continued)

OTHER PUBLICATIONS

1st Office Action of counterpart Chinese Patent Application No. 201510470769.4 dated Mar. 31, 2017.
(Continued)

Primary Examiner — Andrew J Mensh

(57) ABSTRACT

Disclosed is an infusion accessory capable of detecting infusion liquid parameters, which is a lid body, comprising a first portion provided with one or more detecting members and a second portion having one or more liquid channels. Relative position changes may occur between the first portion and the second portion, the liquid channels and the detecting members may be switched between an open position and a closed position as position changes occur between the first portion and the second portion, the open position enables communication between the liquid channels and the detecting members so that liquid in the liquid channels may flow into the detecting members, the close position enables sealing between the liquid channels and the detecting members so that the liquid in the liquid channels cannot flow into
(Continued)

the detecting members and the liquid that already flows into the detecting members cannot return to the liquid channels.

21 Claims, 11 Drawing Sheets

(51) Int. Cl.
*A61M 5/168* (2006.01)
*G01N 33/15* (2006.01)
*A61J 1/06* (2006.01)
*A61M 39/24* (2006.01)

(52) U.S. Cl.
CPC ......... *A61M 5/16854* (2013.01); *G01N 33/15* (2013.01); *A61J 1/065* (2013.01); *A61J 2200/70* (2013.01); *A61M 39/24* (2013.01)

(58) Field of Classification Search
USPC ........................................................ 604/414
See application file for complete search history.

(56) References Cited

U.S. PATENT DOCUMENTS

| | | | | |
|---|---|---|---|---|
| 2009/0118667 | A1* | 5/2009 | Haueter | A61M 5/16854 604/67 |
| 2013/0107267 | A1* | 5/2013 | Leuenberger | A61M 5/14244 356/445 |
| 2014/0094771 | A1* | 4/2014 | Li | A61M 5/14526 604/506 |
| 2014/0273265 | A1* | 9/2014 | Feingold | G01N 27/08 436/163 |
| 2016/0305922 | A1* | 10/2016 | Narang | G01N 13/00 |

FOREIGN PATENT DOCUMENTS

| | | |
|---|---|---|
| CN | 204106691 U | 1/2015 |
| CN | 205235053 U | 5/2016 |

OTHER PUBLICATIONS

2nd Office Action of counterpart Chinese Patent Application No. 201510470769.4 dated Aug. 14, 2017.
3rd Office Action of counterpart Chinese Patent Application No. 201510470769.4 dated Oct. 23, 2017.

* cited by examiner

INFUSION ACCESSORY CAPABLE OF DETECTING INFUSION LIQUID PARAMETERS AND METHOD OF DETECTING INFUSION LIQUID PARAMETERS

FIELD OF THE INVENTION

The invention mainly relates to an infusion accessory, such as an infusion lid body, in particular to an infusion accessory capable of detecting infusion liquid parameters. The invention further relates to a method of detecting infusion liquid parameters by using an infusion accessory.

BACKGROUND OF THE INVENTION

At present stage, the parameters of an infusion liquid formulated before clinical use are generally not detected, because there is no convenient and short time-consuming detection method and device. Each parameter of the infusion liquid formulated before clinical use, such as the pH value, the osmotic pressure and the drug concentration, plays an important role in the clinical treatment quality. However, the existing detection method and device cannot provide a reliable and rapid detection result. During intravenous infusion, the mediums connecting the liquid medicine with the human body are the infusion bottle/bag system and the infusion tube system (such as, an infusion set, a vein/arterial catheter, etc.). The infusion tube is easier to become cross-contaminated, and it is difficult to guarantee that the detection result of each kind of medicine or solution is accurate. Therefore, in order to solve the problem above, it is necessary to find a way in an infusion bottle/bag system, and wherein an infusion bottle cap is the most likely and important accessory to solve the problem above. A sensor or detection assembly can be positioned inside an infusion bottle cap, which can detect the parameters of the infusion liquid rapidly when contacting with the infusion liquid, so as to help guide the clinical treatment.

According to the research about infusion treatment, the important parameters which need to be controlled during a transfusion are the pH value, the electrolysis degree, the osmotic pressure, the concentration of effective component, the insoluble particles and so on. In order to detect one or more parameters, it is necessary to design special sensors or detection devices. Taking the pH value as an example, during each infusion liquid preparation process, it is necessary to monitor whether the pH value is in a range maximizing the medicine efficacy. Based on the data detected by sensors or detection devices, people can adjust the pH value of the infusion liquid so as to maximize the medicine efficacy.

By detecting other data, it is found that different parameters would result in different treatment effects. Infusion reaction and influence factors are investigated based on the principle of evidence-based medicine, and the following table is obtained.

TABLE 1

Medicines of 102 infusion reactions

| kinds of medicine | Cases of infusion reactions | Percentage/% |
|---|---|---|
| none | 17 | 16.7 |
| 1 | 39 | 38.2 |
| 2 | 17 | 16.7 |
| 3 | 12 | 11.8 |
| >3 | 17 | 16.7 |

As what can be seen from Table 1, the percentage of cases using one medicine is the highest (38.2%), meanwhile, about 45% of the cases use two or more than two medicines during infusion treatment in which the infusion parameters cannot be obtained based on the experience, and there is no related research about the infusion parameters of two or more than two medicines at current stage. Therefore, the detection of parameters before transfusion is necessary and has clinical value. Due to the fact that the dosage of the infusion liquid is large, which is generally 100 ml to thousands of milliliters, if a certain parameter changes significantly, then a great influence would be generated on the treatment effect. Although GMP (Good Manufacturing Practice) and GCP (Good Clinical Practice) are enhanced in China recently, accidents of infusion quality should never occur but nevertheless do occur, even adverse drug reactions (ADRs) may occur. The following table shows the occurrence rate of adverse drug reactions.

TABLE 2 cases of ADRs, the drug types and numbers of drugs

| Drug types | Numbers of drugs | Percentage/% | Cases of ADRs | Percentage/% |
|---|---|---|---|---|
| anti-infective drugs | 42 | 41.58 | 155 | 58.49 |
| antipyretic and antalgic drugs | 8 | 7.92 | 17 | 6.41 |
| central nervous system drugs | 10 | 9.90 | 16 | 6.04 |
| digestive system drugs | 5 | 4.95 | 7 | 2.64 |
| respiratory system drugs | 3 | 2.97 | 4 | 1.51 |
| cardiovascular system drugs | 3 | 2.97 | 4 | 1.51 |
| hematological system drugs | 1 | 0.99 | 1 | 0.38 |
| biological products | 5 | 4.95 | 28 | 10.57 |
| antineoplastic drugs | 4 | 3.96 | 5 | 1.89 |
| traditional chinese drugs | 9 | 8.91 | 12 | 4.53 |
| drugs for external Use | 6 | 5.94 | 6 | 2.26 |
| others | 5 | 4.95 | 10 | 3.77 |
| SUM | 101 | 99.99 | 265 | 99.99 |

According to the statistics about the adverse drug reactions shown above, anti-infection drugs lead to more adverse drug reactions, it is found that the super high amount of particles, pyrogen reaction and unsuitable pH value play an important role in adverse reactions caused by anti-infection drugs. All of these parameters are difficult to monitor before transfusion because there is no useful detection device.

The average osmolality of a healthy human body is 298 Osmol/kg, and the normal range of osmolality is 280-310 Osmol/kg. In the way of intravenous transfusion, the infusion liquid directly enters into blood, which has a significant impact on the red blood cells. If the medicine for intravenous transfusion has a low osmotic pressure, the water molecules would penetrate into the red blood cells, causing the rupture of the red blood cells and hemolysis. If the medicine for intravenous transfusion has a high osmotic pressure, the water in the red blood cells would exude, causing the atrophy of the red blood cells. Therefore, the osmotic pressure of the intravenous infusion liquid should be in isotonic condition or slightly higher condition. The Chinese Pharmacopoeia Edition 2000 modified the measurement of osmolality, which clarified that the instruction of an intravenous infusion liquid, a nutrient liquid, an electrolyte liquid or a diuretic agent (such as mannitol injection) should specify the osmolality concentration as a reference for a clinical doctor. Many foreign pharmacopeias also have the same requirement. The cryoscopy is a usual way to detect the osmolality. However, it cannot be performed during or before a transfusion process. There is a great requirement to provide an electronic or non-electronic sensor in the transfusion system to detect the osmolality, so that the parameter can be obtained before a clinical transfusion. According to the literatures, even the same kind of product from different production environments and different manufacturers may have significantly different osmolality, which may cause potential risk in clinical treatment. The glucose and the sodium chloride in the infusion liquid are mainly used to adjust the isotonicity of the product. The amount of the glucose and sodium chloride in a prescription is usually determined by a theoretical calculation. However, the actual osmotic pressure of the product is usually lower than the theoretical calculation due to the interaction between the solute molecules or the solvent molecules. So, the optimal way is to detect the isotonicity of the product before the clinical use to ensure the safety.

SUMMARY OF THE INVENTION

One of the technical problems to be solved by the invention is to provide a real-time, short time-consuming, economical and safe infusion accessory capable of detecting infusion liquid parameters. The infusion accessory of the invention can be used to detect the key parameters of the liquid medicine, such as the pH value, the electrolysis degree, the osmotic pressure, the concentration of effective component and the insoluble particles, and more importantly, the infusion accessory of the invention can be used to detect these key parameters immediately prior to transfusion, so as to help medical staffs to adjust the liquid parameters by some suitable ways and ensure the medicine to be clinically transfused in the optimal parameter range. Based on the parameters of the infusion liquid detected by the infusion accessory of the invention, the medical staffs may have a comprehensive understanding of the key parameters, which is helpful in dispensing or preparing an infusion liquid.

Another technical problem to be solved by the invention is to provide a real-time, short time-consuming, economical and safe method of detecting the infusion liquid parameters.

The above technical problems will be resolved by the following infusion accessory capable of detecting infusion liquid parameters, which is a lid body, comprising a first portion provided with one or more detecting members and a second portion having one or more liquid channels; relative position changes may occur between the first portion and the second portion, the liquid channels of the second portion and the detecting members of the first portion may be switched between an open position and a closed position as position changes occur between the first portion and the second portion, the open position enables communication between the liquid channels and the detecting members so that liquid in the liquid channels may flow into the detecting members; the close position enables sealing between the liquid channels and the detecting members so that it is impossible for the liquid in the liquid channels to flow into the detecting members and the liquid that already flows into the detecting members cannot return to the liquid channels.

The infusion accessory capable of detecting infusion liquid parameters is designed as a lid body, which can be an individual accessory and be assembled to an infusion bottle or an infusion bag to form a complete unit when in use, or can be prepared in one body with an infusion bottle or an infusion bag. Therefore, this infusion accessory is very convenient in clinic application. Preferably, the lid body is prepared in one body with an infusion bottle or an infusion bag, so as to replace the existing lid of an infusion bottle or infusion bag. During a specific clinical application, the infusion accessory, as a lid body, and the infusion bottle or the infusion bag form a complete set, no matter assembled temporarily or present as a complete set as leaving the factory. When the device is not in use, the liquid channels of the second portion and the detection members of the first portion are in a closed state, the detection members cannot be in contact with the liquid; and when the device is in use, the liquid channels of the second portion and the detecting members of the first portion are switched from a closed position to an open position once position changes occur between the first portion and the second portion, and the liquid from the infusion bottle or the infusion bag flows into the detection members through the liquid channels. If position changes occur again between the first portion and the second portion, the liquid channels of the second portion and the detecting members of the first portion can also be switched from an open position to a closed position, so that the liquid that already flows into the detecting members cannot return to the infusion bottle or the infusion bag, so as to avoid polluting the original liquid in the infusion bottle or the infusion bag and ensure the safety. At this time, the detection members show the parameters of the liquid flowing into them. By this way, only a lid body at the opening of an infusion bottle or an infusion bag is needed to detect the parameters of the infusion liquid, and no extra individual medical instrument is required, so it is real-time and convenient, and very helpful in improving the medicine dispensing efficiency in clinics. When an infusion liquid needs to be prepared and detected for many times, more than one detection members can be provided in the first portion, and changing the relative position between the first portion and the second portion after the first detection would enable the liquid channel of the second portion to communicate with another detection member of the first portion, so as to detect the parameters of the infusion liquid freshly prepared once again. In a word, the steps above can be repeated multiple times until all the parameters of the infusion liquid reach the desired values. Because one infusion accessory can be used to detect the parameters for multiple times, the cost of detecting the parameters of the infusion liquid can be significantly reduced. Further, the detection members can be test papers or test reagents which cost quite low. Therefore, the present invention discloses an economic and efficient infusion accessory and method. In addition, multiple detection members can be provided in the first portion, and changing the relative position between the first portion and the second portion would enable the liquid channel of the second portion to communicate with the multiple detection members one after another, so as to detect multiple different parameters by using the multiple different detection members. In this invention, only a little liquid, even a drop of liquid, is required for each detection, so it avoids wasting the liquid medicine. Furthermore, there is no need to puncture the infusion bottle or the infusion bag to get the liquid inside, so chippings which are generally generated by puncture in the prior art are avoided.

The invention provides an alternative solution of the infusion accessory capable of detecting infusion liquid parameters, wherein the first portion is a first ring body, the annular wall of the first ring body is provided with one or more containing chambers, and the detection members are arranged in the containing chambers of the annular wall of the first ring body; and the second portion is a second ring body which can be rotated concentrically relative to the first ring body, and the liquid channels are arranged in the annular wall of the second ring body; the liquid channels of the second ring body and the containing chambers of the first ring body can be switched between an open position and a closed position as the second ring body is rotated concentrically relative to the first ring body.

When in use, the second ring body is simply rotated to switch the liquid channels of the second ring body and the containing chamber of the first ring body between an open position and a closed position. By adopting the structural form of the concentric ring bodies, it is very convenient to perform the rotation operation, so as to facilitate the clinical application.

Further, the second ring body is disposed above the first ring body, and the containing chamber of the first ring body is a slot or cavity axially arranged in the annular wall of the first ring body, and the liquid channel of the second ring body is arranged to be vertical or inclined channel. In an open position, the liquid in the vertical or inclined channel flows into the detecting member arranged in the slot or cavity. The vertical or inclined channel can prevent the liquid that already flows into the slot or cavity from returning to the liquid channel.

Preferably, there are multiple axial slots or cavities along the annular wall of the first ring body, and the liquid channels and the multiple slots or cavities are sequentially witched between an open position and a closed position as the second ring body is rotated concentrically relative to the first ring body. Since the first portion is provided with multiple slots or cavities containing the detection members, the liquid channel of the second portion can communicate with the slots or cavities of the first portion one after another, so as to perform multiple comparative tests and detect different liquid parameters, which is helpful in improving the medicine dispensing efficiency and reducing the detection cost in clinical practice. Therefore, the present invention has obvious economical advantages compared with the prior art.

The invention also provides another alternative solution of an infusion accessory capable of detecting infusion liquid parameters, wherein the first portion is mobile, and the second portion is immobilized. The first portion is a first ring body, and the annular wall of the first ring body is provided with one or more containing chambers, and the detection members are arranged in the containing chambers of the annular wall of the first ring body; and the second portion is a second ring body, and one or more liquid channels are arranged in the annular wall of the second ring body, the first ring body can be rotated concentrically relative to the second ring body; the liquid channels of the second ring body and the containing chambers of the first ring body can be switched between an open position and a closed position as the first ring body is rotated concentrically relative to the second ring body.

During use, the first ring body is simply rotated to switch the liquid channels of the second ring body and the containing chamber of the first ring body between an open position and a closed position.

Further, the second ring body is sleeved on the first ring body, wherein the containing chamber comprises a slot or cavity axially arranged in the annular wall of the first ring body and a first through hole radially arranged in the annular wall of the first ring body, and the liquid channels are arranged in the inner surface of the annular wall of the second ring body. In an open position, the liquid in the liquid channels flows into the axial slot or cavity through the first through hole radially arranged in the annular wall of the first ring body and is detected by the detecting members in the slot or cavity.

Preferably, a plurality of slots or cavities are axially arranged and a plurality of first through holes corresponding to the respective slots or cavities are radially arranged in the annular wall of the first ring body, and the liquid channels and the first through holes are switchable between an open position and a closed position as the first ring body is rotated concentrically relative to the second ring body. The liquid channels of the second portion may sequentially communicate with the plurality of cavities of the first portion when the position of the first portion is changed relative to the second portion, so that multiple comparison tests and detections can be performed, or different liquid parameters can be detected, thereby improving the dispensing efficiency and reducing the cost for detection in clinical practice. Therefore, the present invention has a significant economic efficiency over the prior art.

Preferably, according to the present invention, in an open position, a backflow prevention structure is formed between an opening of the liquid channels of the second ring body and an opening of the containing chambers of the first ring body so that a portion of the liquid that has flowed into the containing chamber is prevented from flowing back to the liquid channels. For example, in an open position, the opening of the liquid channels is only partially communicated with the opening of the containing chamber, and the lowest point of the opening of the liquid channels is higher than the lowest point of the opening of the containing chamber, so that a height difference is formed to prevent the liquids that have flowed into the containing chamber from flowing back to the liquid channels. In an open position, when the opening of the liquid channels is only in partial communication with the opening of the containing chamber, the liquid in the liquid channels may flow or even drop slowly into the containing chamber instead of flowing quickly into the containing chamber which may result in a backflow.

Particularly, the detecting members may be test papers or detection reagents, and other detecting members that are easily disposed in a small cavity may also be used.

The present invention provides another improvement of the infusion accessory capable of detecting infusion liquid parameters. The first portion is a first ring body, wherein the detecting members are arranged on an outer surface of the first ring body, and the second through-holes in communication with the detecting members are formed in an annular wall of the first ring body. The second portion is a second ring body which is rotatable concentrically with respect to the first ring body, wherein the liquid channels are arranged in an annular wall of the second ring body. The first ring body is sleeved on an outer surface of the second ring body, and the liquid channels of the second ring body and the second through-holes of the first ring body are switchable between an position and a closed position as the second ring body is rotated concentrically with respect to the first ring body.

Further, the liquid channel comprise a slot formed along the annular wall of the second ring body in an axial direction and a third through hole formed along the annular wall of the second ring body in a radial direction. In an open position, the liquid flows into the third through hole through the slot and then flows into the second through hole in the annular wall of the first ring body to flow into the detecting members for detection. In addition, the liquid channel may be a through hole formed along the annular wall of the second ring body in a radial direction, and the axial slot is unnecessary. Preferably, the annular wall of the second ring body is provided with a plurality of liquid channels. In a word, a plurality of slots are axially arranged and a plurality of third through holes corresponding to the respective slots are radially arranged in the annular wall of the second ring body. The third through holes of the second ring body are successively aligned with the second through holes of the first ring body as the second ring body is rotated concentrically with respect to the first ring body, so that the liquid flows into the detecting members successively.

Particularly, the detecting member is a color-developing sensor.

The present invention provides a further improvement of the infusion accessory capable of detecting infusion liquid parameters. The first portion is a first ring body, wherein a plurality of annular are arranged between an inner surface and an outer surface of an annular wall of the first ring body in a circumferential direction, and a height of the multiple annular grooves increases progressively from the inner surface to the outer surface with a gradient form, and notches are formed in the inner surface of the annular wall of the first ring body, and the detection members are arranged in the annular grooves. The second portion is a second ring body which is rotatable concentrically with respect to the first ring body, and the first ring body is sleeved on an outer surface of the second ring body. The liquid channels are arranged on the annular wall of the second ring body; and the liquid channels of the second ring body and the notch of the first ring body are switchable between an open position and a closed position as the second ring body is rotated concentrically with respect to the first ring body.

Further, the liquid channel comprises a slot formed along the annular wall of the second ring body in an axial direction and a fourth through hole formed along the annular wall of the second ring body in a radial direction. In an open position, the liquid flows into the fourth through hole through the slot, and then flows into the notch of the first ring body, thereby flowing into the annular grooves. Additionally, the liquid channes may be a through hole formed along the annular wall of the second ring body in a radial direction, and the axial slot of the liquid channel is unnecessary.

Preferably, a plurality of slots are axially arranged and a plurality of fourth through holes corresponding to the respective slots are radially arranged on the annular wall of the second ring body, wherein the opening heights of the plurality of fourth through holes successively correspond to the heights of the plurality of annular grooves, respectively. During use, one fourth through-hole located at the lower position is firstly communicated with the notch, and the liquid flows into the first annular groove with the lowest height; as the second ring body continues to be rotated, the communication between the fourth through hole 4023 and the notch is closed; if the second ring body is rotated continuously, another fourth through hole 3 located at the higher position would communicate with the notch, and the liquid flows into the second annular groove of which the height is higher than that of the first annular groove. Such operations are repeated to achieve multiple detections.

The present invention further provides an alternative infusion accessory for detecting infusion liquid parameters.

The infusion accessory capable of detecting infusion liquid parameters is a lid body, comprising a first portion provided with one or more detecting members and a second portion provided with one or more liquid channels. The second portion is a ring body, and the liquid channels are arranged in an annular wall of the second portion. The first portion is a reverse check valve device which is connected to the annular wall of the second ring body and is able to extract liquid from the liquid channels of the second ring body, and the detection members are arranged in the reverse check valve device; when the reverse check valve extracts liquid from the liquid channels, the liquid channels of the second ring body and the detecting members in the reverse check valve are switched in an open position, which enables liquid the liquid channels to flow into the detection members; when the reverse check valve stops extracting liquid from the liquid channels, the liquid channels of the second ring body and the detecting members in the reverse check valve are switched in a close position, so that it is impossible for the liquid in the liquid channels to flow into the detecting members and the liquid that already flows into the detecting members cannot return to the liquid channels. Such an infusion accessory has a simple structure and is easy to mold and assemble; however, the reverse check valve device is expensive and costly.

The infusion accessory capable of detecting infusion liquid parameters according to the invention can be attached to an infusion bottle or bag and may also comprise an outer cover with a sealing assembly for sealing the lid body. The outer cover can be a standard and conventional cap of the existing infusion bottles or infusion bags, so the infusion accessory of the present invention can be integrated with the existing infusion bottles or infusion bags. As a result, the infusion accessory of the present invention is easy to spread the use of it. Specifically the lid body is made of transparent material so that the detection condition in the cavity can be clearly observed.

The present invention also provides a method of detecting infusion liquid parameters using an infusion accessory:

the infusion accessory is a lid body, comprising an outer cover with a seal assembly for sealing the lid body, and a first portion provided with one detecting member and a second portion having one liquid channel;

wherein relative position changes occur between the first portion and the second portion when an external force is applied, the liquid channel of the second portion and the detecting member of the first portion are switched between an open position and a closed position as position changes occur between the first portion and the second portion, the open position enables communication between the liquid channel and the detecting member so that liquid in the liquid channel flows into the detecting member, and the close position enables sealing between the liquid channel and the detecting member so that it is impossible for the liquid in the liquid channel to flow into the detecting member and the liquid that already flows into the detecting member cannot return to the liquid channel;

and the method comprises the following steps of:

connecting the infusion accessory to an infusion bottle or an infusion bag, so that the liquid channel of the second portion of the infusion accessory is in fluid communication with liquid in the infusion bottle or the infusion bag;

changing relative position between the second portion and the first portion, so that the liquid channel of the second portion is in communication with the detecting member of the first portion, and liquid in the liquid channel flows into the detecting member;

changing relative position between the second portion and the first portion again, so that the communication between the liquid channel and the detection member is closed;

detecting the parameter of the liquid flowing into the detecting member by the detection member.

In this method, the infusion accessory used herein can be individual and be temporarily assembled to an infusion bottle or an infusion bag to form a complete unit when in use, or can be prepared in one body with an infusion bottle or an infusion bag. Preferably, the infusion accessory is prepared in one body with an infusion bottle or an infusion bag, sa as to replace the conventional lid of the infusion bottle or bag in the prior art.

The present invention also provides another method of detecting infusion liquid parameters by using an infusion accessory:

the infusion accessory is a lid body, comprising a first portion provided with multiple detecting members and a second portion having one liquid channel, wherein the multiple detecting members are used to detect the same parameter;

wherein relative position changes occur between the first portion and the second portion when an external force is applied, the liquid channel of the second portion and the detecting members of the first portion are switched between an open position and a closed position as position changes occur between the first portion and the second portion, the open position enables communication between the liquid channel and one of the detecting members so that liquid in the liquid channel flows into the detecting member, and the close position enables sealing between the liquid channel and the detecting members so that it is impossible for the liquid in the liquid channel to flow into the detecting members and the liquid that already flows into the detecting members cannot return to the liquid channel;

the method comprises the following steps of:

connecting the infusion accessory to an infusion bottle or an infusion bag, so that the liquid channel of the second portion of the infusion accessory is in fluid communication with liquid in the infusion bottle or the infusion bag;

changing relative position between the second portion and the first portion, so that the liquid channel of the second portion is in communication with a first detecting member of the first portion, and liquid in the liquid channel flows into the first detecting member;

changing relative position between the second portion and the first portion again, so that the communication between the liquid channel and the first detection member is closed;

detecting the parameter of the liquid flowing into the first detecting member by the first detection member;

adding new liquid medicine into the infusion bottle or the infusion bag to adjust the parameter of the liquid in the infusion bottle or the infusion bag if the detected parameter of the infusion liquid fails to reach the desired value;

changing relative position between the second portion and the first portion again after addition of new liquid medicine, so that the liquid channel of the second portion is in communication with a second detecting member of the first portion, and liquid in the liquid channel flows into the second detecting member;

changing relative position between the second portion and the first portion again, so that the communication between the liquid channel and the second detection member is closed;

detecting the parameter of the liquid flowing into the second detecting member by the second detection member;

adding new liquid medicine into the infusion bottle or the infusion bag to adjust the parameter of the liquid in the infusion bottle or the infusion bag if the detected parameter of the infusion liquid still fails to reach the desired value, and repeating the above steps until the parameter of the liquid in the infusion bottle or the infusion bag reaches the desired value.

The present invention also provides the third method of detecting infusion liquid parameters by using an infusion accessory:

The infusion accessory is a lid body, comprising a first portion provided with multiple detecting members and a second portion having one liquid channel, wherein the multiple detecting members are different and are used to detect different parameters;

wherein relative position changes occur between the first portion and the second portion when an external force is applied, the liquid channel of the second portion and the detecting members of the first portion are switched between an open position and a closed position as position changes occur between the first portion and the second portion, the open position enables communication between the liquid channel and one of the detecting members so that liquid in the liquid channel flows into the detecting member, and the close position enables sealing between the liquid channel and the detecting members so that it is impossible for the liquid in the liquid channel to flow into the detecting members and the liquid that already flows into the detecting members cannot return to the liquid channel;

the method comprises the following steps of:

connecting the infusion accessory to an infusion bottle or an infusion bag, so that the liquid channel of the second portion of the infusion accessory is in fluid communication with liquid in the infusion bottle or the infusion bag;

changing relative position between the second portion and the first portion, so that the liquid channel of the second portion is in communication with a first detecting member of the first portion, and liquid in the liquid channel flows into the first detecting member;

changing relative position between the second portion and the first portion again, so that the communication between the liquid channel and the first detection member is closed;

detecting a first parameter of the liquid flowing into the first detecting member by the first detection member;

changing relative position between the second portion and the first portion again, so that the liquid channel of the second portion is in communication with a second detecting member of the first portion, and liquid in the liquid channel flows into the second detecting member;

changing relative position between the second portion and the first portion again, so that the communication between the liquid channel and the second detection member is closed;

detecting a second parameter of the liquid flowing into the second detecting member by the second detection member;

repeating the above steps until all desired parameters of the liquid are detected.

REFERENCE NUMBERS

Figure 1:
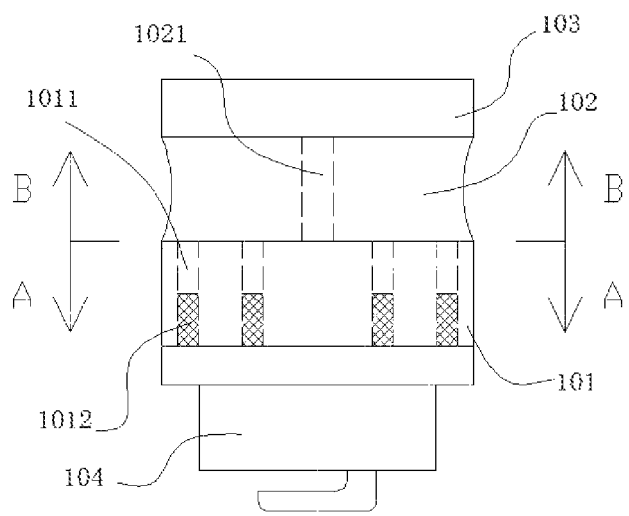
FIG. 1 is a cross-sectional view of an infusion accessory according to Example 1 of the present invention.

Example 1: first ring body 101, cavity 1011, detection member 1012, second ring body 102, liquid channel 1022, fixed base 103, outer cover 104.

Example 2: first ring body 201, containing chamber 2011, slot 2012, first through-hole 2013, second ring body 202, liquid channel 2021, height difference 2022, outer cover 204, infusion bottle 205.

Example 3: first ring body 301, second through-hole 3011, detection member 3012, second ring 302, liquid channel 3021, slot 3022, third through hole 3023, height difference 3024, outer cover 304, infusion bottle 305.

Example 4: first ring body 401, annular grooves 4011, 40111, 40112, notch 4012, second ring body 402, liquid channel 4021, slot 4022, third through-hole 4023, outer cover 404, infusion bottle 405.

Example 5: ring body 502, reverse check valve 501.

DETAILED DESCRIPTION OF ILLUSTRATED EMBODIMENTS

Hereinafter, the present invention will be described in more detail with reference to the following embodiments. It is to be understood, one or more aspects and embodiments may be incorporated in a different embodiment although not specifically described. That is, all aspects and embodiments can be combined in any way or combination. As used herein, the singular forms "a," "an", and "the" include plural references unless the context clearly dictates otherwise.

The invention discloses an infusion accessory capable of detecting infusion liquid parameters, which is a cover body, comprising a first portion provided with one or more detecting members and a second portion having one or more liquid channels; wherein relative position changes may occur between the first portion and the second portion, the liquid channels of the second portion and the detecting members of the first portion may be switched between an open position and a closed position as position changes occur between the first portion and the second portion, the open position enables communication between the liquid channels and the detecting members so that liquid in the liquid channels flows into the detecting members, and the close position enables sealing between the liquid channels and the detecting members so that it is impossible for the liquid in the liquid channels to flow into the detecting members and the liquid that already flows into the detecting members cannot return to the liquid channels.

The infusion accessory capable of detecting infusion liquid parameters is designed as a lid body, which can be an individual accessory and be assembled to an infusion bottle or an infusion bag to form a complete unit when in use, or can be prepared in one body with an infusion bottle or an infusion bag. Therefore, this infusion accessory is very convenient in clinic application.

During a specific clinical application, the infusion accessory, as a lid body, and the infusion bottle or the infusion bag form a complete set, no matter assembled temporarily or present as a complete set as leaving the factory. When the device is not in use, the liquid channels of the second portion and the detection members of the first portion are in a closed state, the detection members cannot be in contact with the liquid; and when the device is in use, the liquid channels of the second portion and the detecting members of the first portion are switched from a closed position to an open position once position changes occur between the first portion and the second portion, and the liquid from the infusion bottle or the infusion bag flows into the detection members through the liquid channels. If position changes occur again between the first portion and the second portion, the liquid channels of the second portion and the detecting members of the first portion can also be switched from an open position to a closed position, so that the liquid that already flows into the detecting members cannot return to the infusion bottle or the infusion bag, so as to avoid polluting the original liquid in the infusion bottle or the infusion bag and ensure the safety. At this time, the detection members show the parameters of the liquid flowing into them. By this way, only a lid body at the opening of an infusion bottle or an infusion bag is needed to detect the parameters of the infusion liquid, and no extra individual medical instrument is required, so it is real-time and convenient, and very helpful for improving the medicine dispensing efficiency in clinics. When an infusion liquid needs to be prepared and detected for many times, more than one detection members can be provided in the first portion, and changing the relative position between the first portion and the second portion after the first detection would enable the liquid channel of the second portion to communicate with another detection member of the first portion, so as to detect the parameters of the infusion liquid freshly prepared. In a word, the steps above can be repeated multiple times until all the parameters of the infusion liquid reach the desired values. Because one infusion accessory can be used to detect the parameters for multiple times, the cost of detecting the parameters of the infusion liquid can be significantly reduced. Further, the detection members can be a test paper or a test reagent which costs quite low. Therefore, the present invention discloses an economic and efficient infusion accessory and method. In addition, multiple detection members can be provided in the first portion, and changing the relative position between the first portion and the second portion would enable the liquid channel of the second portion to communicate with the multiple detection members one after another, so as to detect multiple different parameters by using the multiple different detection members. In this invention, only a little liquid, even a drop of liquid, is required in each detection, so it avoids wasting the liquid medicine. Furthermore, there is no need to puncture the infusion bottle or the infusion bag to get the liquid inside, so chippings which are generally generated by puncture in the prior art are avoided.

Example 1

Figure 2:
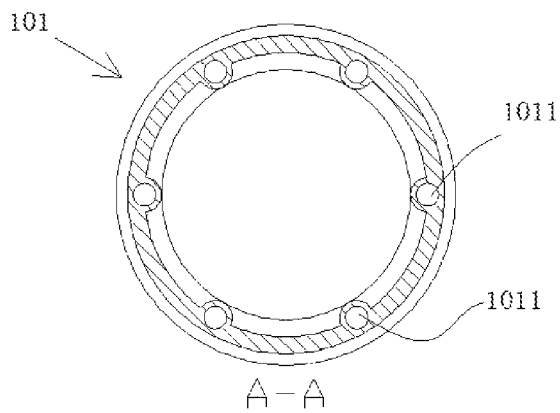
FIG. 2 is a cross-sectional view of Example 1 in FIG. 1 along direction A-A, showing a first ring body being immobilized.
Figure 3:
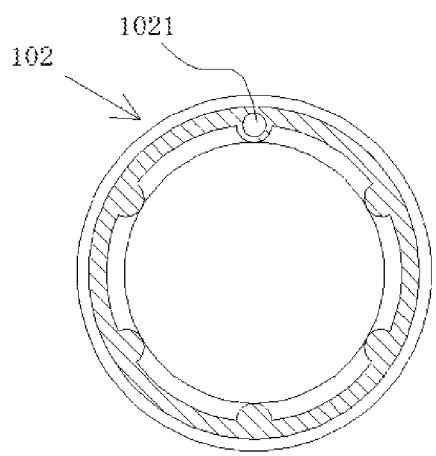
FIG. 3 is a cross-sectional view of Example 1 in FIG. 1 along direction B-B, showing a second ring body which is rotatable.
Figure 4:
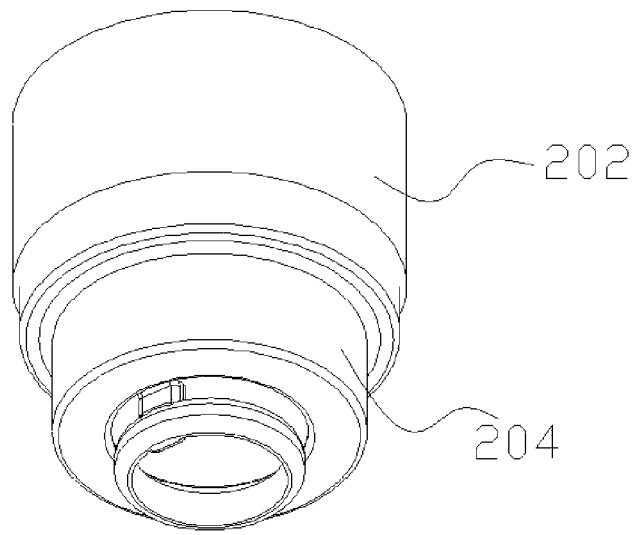
FIG. 4 is a stereo view of an infusion accessory according to Example 2 of the present invention.

In Example 1, as shown in FIGS. 1-3, the first portion is a first ring body 101, the annular wall of the first ring body 101 is provided with containing chambers 1011, the detection members 1012 are arranged in the containing chambers 1011. The containing chambers 1011 are cavities axially arranged in the annular wall of the first ring body 101. The second portion is a second ring body 102 which can be rotated concentrically relative to the first ring body 101, the liquid channel 1021 is arranged in the annular wall of the second ring body 102. The liquid channel 1021 of the second ring body 102 and the containing chamber 1011 of the first ring body 101 can be switched between an open position and a closed position as the second ring body 102 is rotated concentrically relative to the first ring body 101. The bending arrow in FIG. 3 shows the rotatable second ring body 102.

The containing chambers 1011 is not in contact with the liquid when the device is not in use (that is, the liquid channel 1021 of the second ring body 102 and the containing chamber 1011 of the first ring body 101 is in a closed position). When the device is in use, as the second ring body 102 being rotated, the liquid channel 1021 of the second ring body 102 would be communicated with the containing chambers 1011 of the first ring body 101 one after another, so that the liquid can sequentially enter into the multiple containing chambers 1011 of the first ring body 101. The detection members 1012 are arranged in the containing chambers 1011, once the liquid medicine enters the containing chambers 1011, it cannot return to the original liquid. When an infusion liquid needs to be prepared and detected for many times, the second ring body 102 can be rotated to communicate with the next containing chamber 1011 following the last detection, then the newly-prepared liquid flows into the unused containing chamber 1011, so as to detect the new parameters by the unused containing chamber 1011, and the operation can be repeated until the desired parameters are finally reached. The first ring body 101 and the second ring body 102 are assembled in a structural form of concentric ring bodies, which can be rotated and operated conveniently. So, the device is convenient in clinical application.

Preferably, the second ring body 102 is arranged above the first ring body 101. The liquid channel 1021 of the second ring body 102 is a vertical or inclined channel, which is in favor of preventing liquid flowing into the containing chamber 1011 from returning to the liquid channel 1021. In addition, the liquid in the vertical or inclined channel would flow or drip slowly into the containing chamber 1011 instead of flowing quickly into the containing chamber 1011 which may result in a backflow.

Preferably, in an open position, the opening of the liquid channel 1021 of the second ring body 102 is only in partial communication with the opening of the containing chamber 1011 of the ring body 101. This arrangement enables the liquid in the liquid channel to flow slowly even drop into the containing chamber 1011 instead of flowing instantly into the containing chamber 1011, which may result in the liquid returning to the infusion bottle or infusion bag.

Preferably, as an alternative of the example, the outer circumference surface of the upper part of the first ring body 101 has an extension part extending upward, which is tightly mated with the outer circumference surface of the lower part of the second ring body 102, so as to seal the joint part of the second ring body 102 and the first ring body 101. By this way, the first ring body 101 and the second ring body 102 form a muff-coupling structure. Sealing the joint part of the first ring body 101 and the second ring body 102 by the extension part enables interior sealing of the infusion accessory, so as to avoid external pollution and prevent the liquid from flowing out.

In other embodiments, the outer circumference surface of the lower part of the second ring body 102 has an extension part extending downward, which is tightly mated with the outer circumference surface of the upper part of the first ring body 101, so as to seal the joint part of the second ring body 102 and the first ring body 101. By this way, the first ring body 101 and the second ring body 102 form a muff-coupling structure.

In this example, the detection member 1012 can be a test paper or a detection reagent. Other appropriate detection members which are convenient to be arranged in a narrow cavity can also be considered in other embodiments.

The upper portion of the infusion accessory is arranged with a fixed base 103 which can be tightly mated with an infusion bottle or infusion bag, and the lower portion of the infusion accessory is arranged with an outer cover 104 with a seal assembly for sealing the lid body. The fixed base 103 and the outer cover 104 mentioned above can be conventional structures for the caps of the existing infusion bottles or infusion bags, so the infusion accessory of the present invention can be integrated with the existing infusion bottles or infusion bags. As a result, the infusion accessory of the present invention is easy to spread the use of it. In addition, the outer cover with a seal assembly can isolate the interior of the lid body from the exterior to ensure the interior of the lid body safe, clean and pollution-free. In this embodiment, the lid body is made of transparent material so that the detection condition in the cavity can be clearly observed.

Example 2

The main difference between example 2 and example 1 is as follows: in example 2, the first ring body can be rotated relative to the second ring body and the second ring body is immobilized, rather than the first ring body is immobilized and the second ring body is mobile. As shown in FIGS. 4-11, in example 2, the first portion is a first ring body 201, the containing chambers 2011 are arranged in the annular wall of the first ring body 201, and the detection members are arranged in the containing chamber 2011 of the first ring body 201; the second portion is a second ring body 202, and the liquid channel 2021 is arranged in the annular wall of the second ring body 202; the first ring body 201 can be rotated concentrically relative to the second ring body 202, and the liquid channel 2021 of the second ring body 202 and the containing chamber 2011 of the first ring body 201 can be switched between an open position and a closed position as the first ring body 201 is rotated concentrically relative to the second ring body 202.

Figure 5:
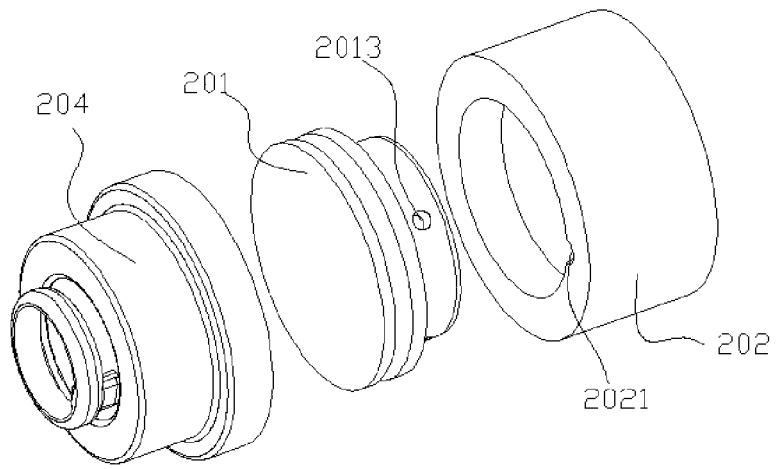
FIG. 5 is an exploded view of an infusion accessory according to Example 2 of the present invention.
Figure 6:
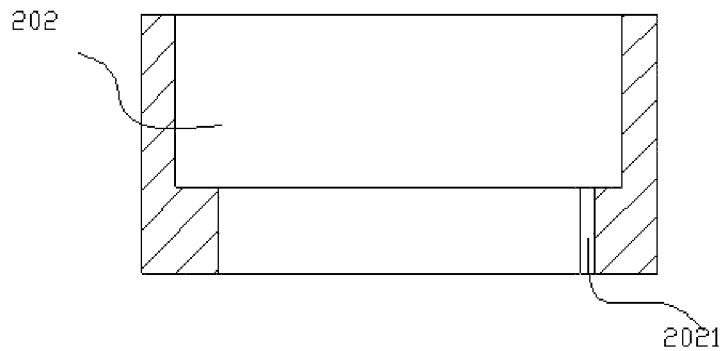
FIG. 6 is a cross-sectional view of a second ring body according to Example 2 of the present invention.
Figure 7:
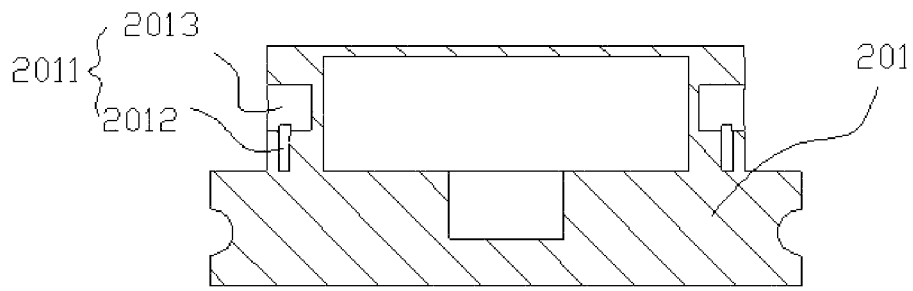
FIG. 7 is a cross-sectional view of a first ring body according to Example 2 of the present invention.
Figure 8:
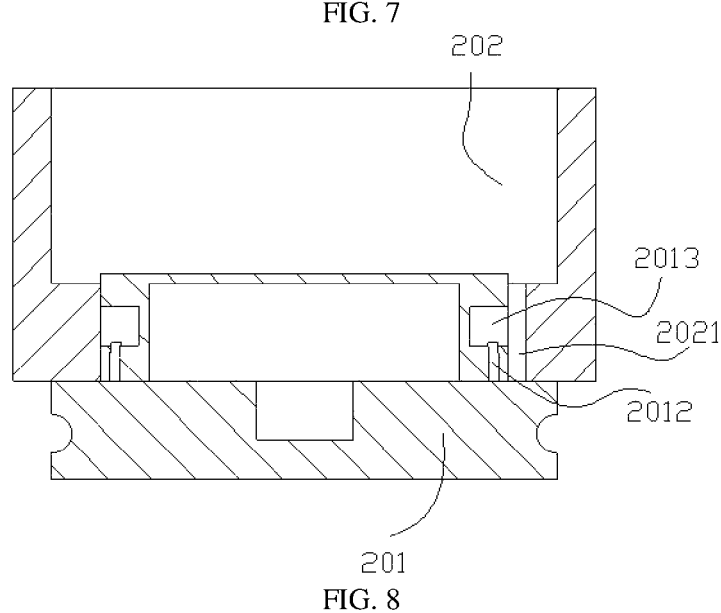
FIG. 8 is a cross-sectional view of the assembled second ring body and first ring body according to Example 2 of the present invention.

Specifically, as shown in FIG. 5, the second ring body 202 is sleeved on the first ring body 201, and as shown in FIG. 7, the containing chamber 2011 comprises a slot 2012 and a first through-hole 2013, wherein the slot 2012 is axially arranged in the annular wall of the first ring body 201 and the first through-hole 2013 is radially arranged in the annular wall of the first ring body 201. As shown in FIG. 6, the liquid channel 2021 is arranged in the inner surface of the annular wall of the second ring body 202. When in use, the liquid channel 2021 of the second ring body 202 and the first through-hole 2013 of the containing chamber 2011 of the first ring body 201 can be switched between an open position and a closed position by rotating the first ring body 201. As shown in FIG. 8, in an open position, the liquid in the liquid channel 2021 flows into the slot 2012 through the first through-hole 2013, then the liquid parameters are detected by the detection members in the slot 2012. In this embodiment, the detection members can be a detection test paper or a detection reagent which is low in cost.

Preferably, multiple slots and multiple first through-holes corresponding to the respective slots are arranged in the annular wall of the first ring body 201, the liquid channel 2021 and the multiple first through-holes 2013 can be sequentially switched between an open position and a closed position as the first ring body 201 is rotated concentrically relative to the second ring body 202. While the first ring body 201 is rotated relative to the second ring body 202 in sequence, the liquid channel 2021 of the second ring body 202 can communicate with the slots 2012 of the first ring body 201 one by one. By this way, one infusion accessory can be used to detect the parameters for multiple times, which contributes to improve the medicine dispensing efficiency and reduce the detection cost in clinical practice. Therefore, the present invention has obvious economical advantages compared with the prior art.

Figure 9:
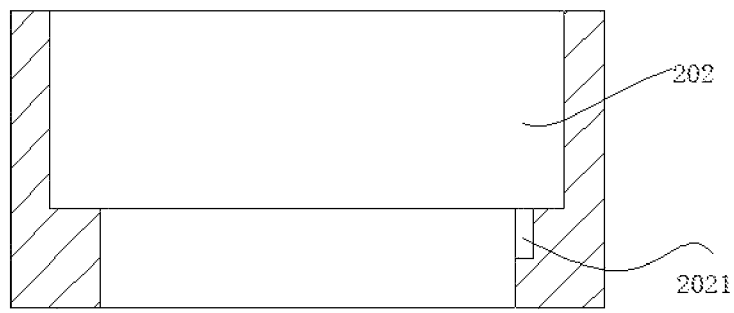
FIG. 9 is a cross-sectional view of a variation of the second ring body according to Example 2 of the present invention.
Figure 10:
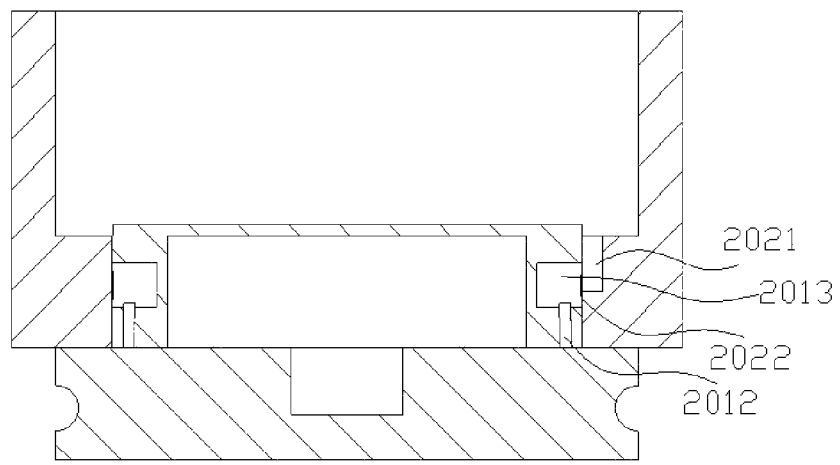
FIG. 10 is a cross-sectional view of the assembled second ring body of FIG. 9 and first ring body.

As an alternative of this example, as shown in FIG. 9 and FIG. 10, when the liquid channel 2021 of the second ring body 202 and one of the containing chambers 2011 of the first ring body 201 are switched in an open position, a backflow prevention structure is formed between the opening of the liquid channel 2021 and the opening of the containing chambers 2011, which can prevent the liquid that already flows into the containing chambers 2011 from returning to the liquid channel 2021. It can be seen from FIG. 10 that the lowest point of the liquid channel 2021 is slightly higher than the lowest point of the opening of the first through-hole 2013, so that a height difference 2022 is formed. The height difference 2022 can prevent the liquid flowing into the first through-hole 2013 from returning to the liquid channel 2021, so as to avoid pollution of the liquid medicine in the infusion bottle or the infusion bag. Meanwhile, in an open position, the opening of the liquid channel 2021 is only in partial communication with the opening of the containing chamber 2011. Specifically, as shown in FIG. 8 and FIG. 9, in an open position, the first through-hole 2013, that is the opening of the containing chamber 2011, and the liquid channel 2021 are not completely communicated with each other, the lowest point of the liquid channel 2021 is slightly higher than the lowest point of the opening of the first through hole 2013, so they are only partially communicated with each other. When the communication space is small enough (for example, as small as a narrow gap), in an open position, the liquid in the liquid channel 2021 would slowly into the first through-hole 2013 instead of flowing instantly into the through-hole 2013, which may result in the liquid that already flows into the first through hole 2013 flowing or splashing back to the infusion bottle or infusion bag under an impact force.

Figure 11:
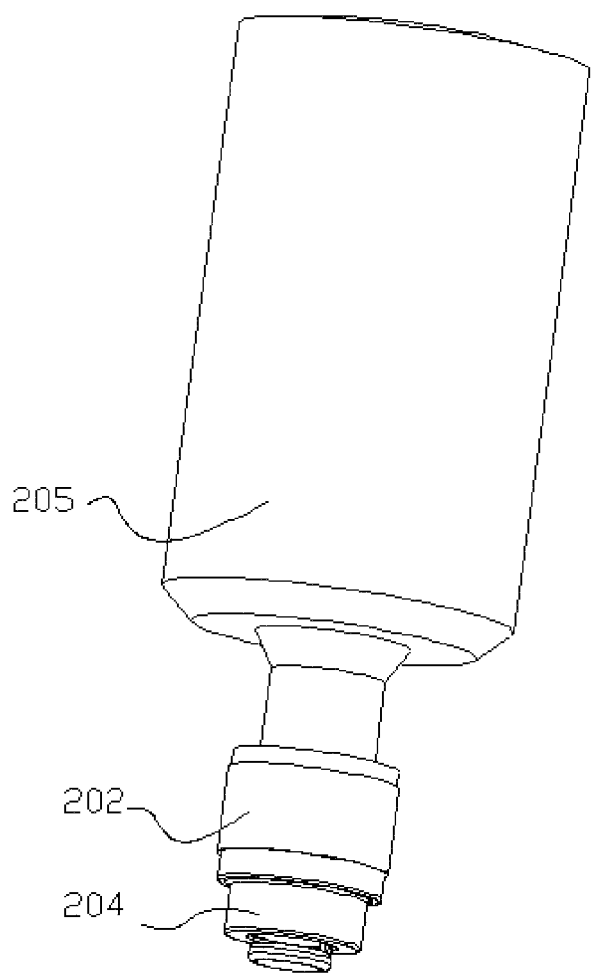
FIG. 11 is a schematic diagram of an infusion accessory according to Example 2 of the present invention being assembled with an infusion bottle.
Figure 12:
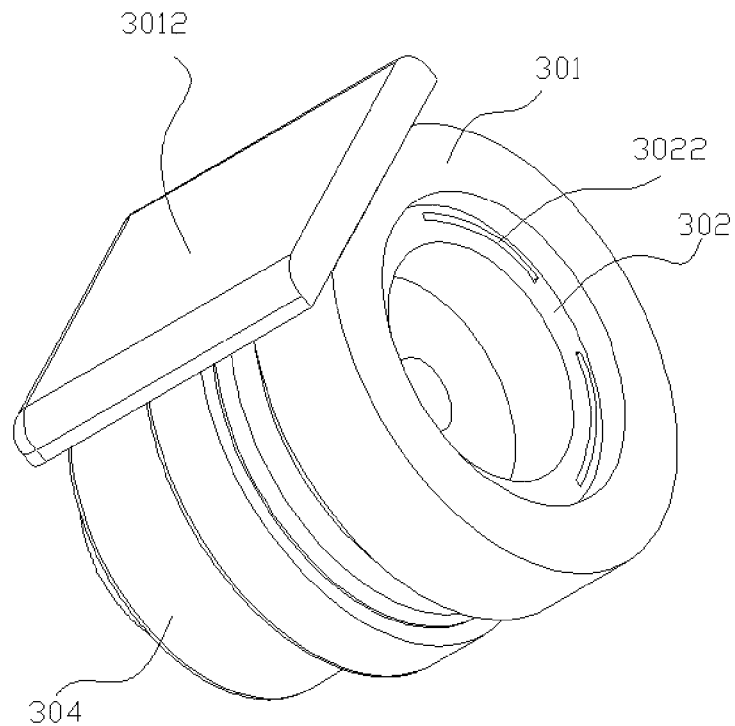
FIG. 12 is a stereo view of an infusion accessory according to Example 3 of the present invention.
Figure 13:
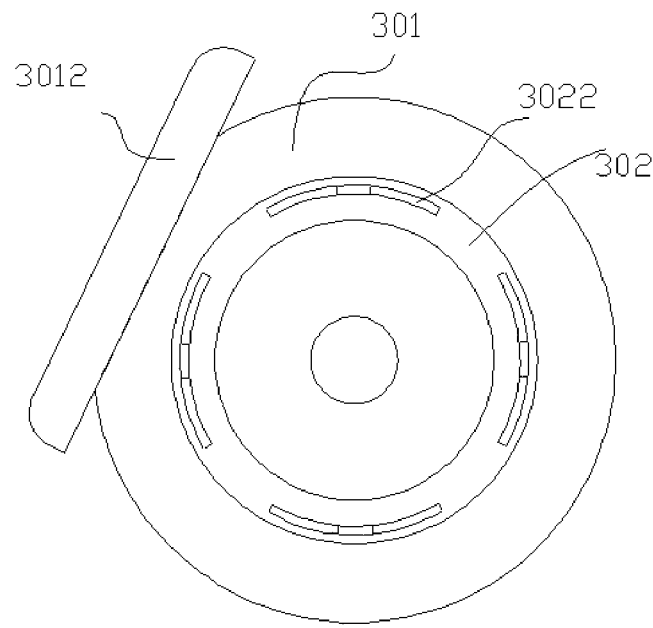
FIG. 13 is a bottom view of an infusion accessory according to Example 3 of the present invention.
Figure 14:
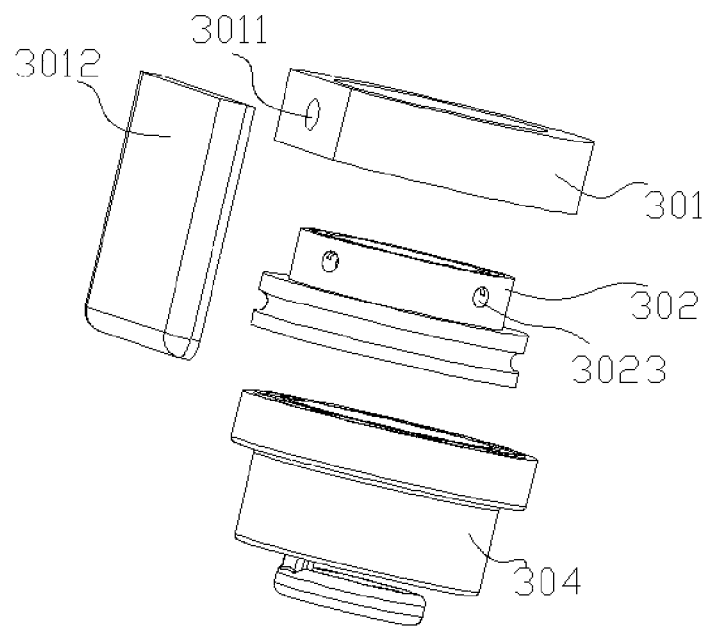
FIG. 14 is an exploded view of an infusion accessory according to Example 3 of the present invention.
Figure 15:
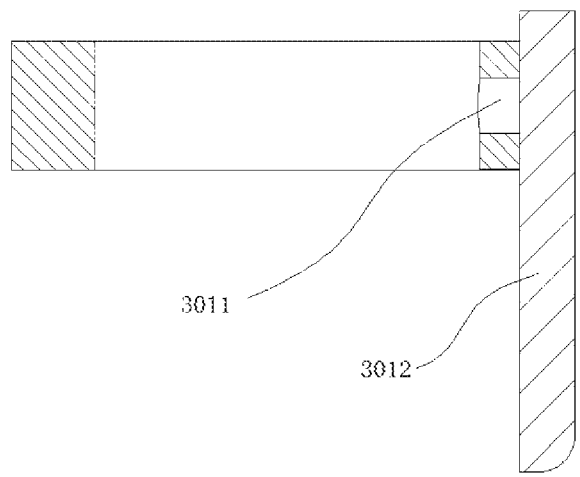
FIG. 15 is a cross-sectional view of a first ring body according to Example 3 of the present invention.
Figure 16:
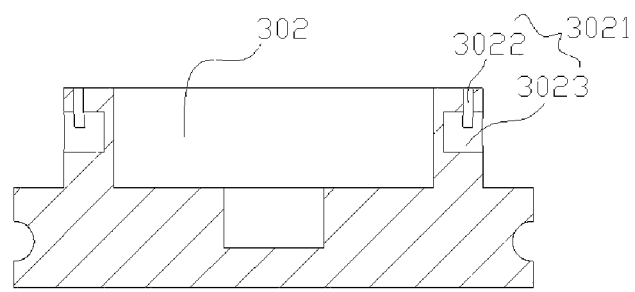
FIG. 16 is a cross-sectional view of a second ring body according to Example 3 of the present invention.

In this embodiment, the second ring body 202 is mounted to an opening of an infusion bottle or infusion bag. An outer cover 204 with a seal assembly for sealing the lid body is arranged at the bottom of the second ring body 202, and the outer cover 204 is sleeved on the lower part of the first ring body 201 and fixedly connected with the first ring body 201. When the outer cover 204 being rotated, the first ring body 201 is driven to rotate concentrically relative to the second ring body 202. The outer cover 104 can be a standard and conventional cap of the existing infusion bottles or infusion bags, so the infusion accessory of the present invention can be integrated with the existing infusion bottles or infusion bags. As a result, the infusion accessory of the present invention is easy to spread the use of it. In addition, the out cover with a seal assembly can isolate the interior of the lid body from the exterior to ensure the interior of the lid body safe, clean and pollution-free. FIG. 11 shows the infusion accessory of the present invention assembling with an infusion bottle 205 to form a complete set.

Example 3

As shown in FIGS. 12-19, in this embodiment, the first portion is a first ring body 301, the detection member 3012 is arranged on the outer surface of the first ring body 301, and a second through-hole 3011 communicating with the detection member 3012 is arranged in the annular wall of the first ring body 301; the second portion is a second ring body 302 which can be rotated concentrically relative to the first ring body 301, and the liquid channel 3021 is arranged in the annular wall of the second ring body 302; and the first ring body 301 is sleeved on the outer surface of the second ring body 302, the liquid channel 3021 of the second ring body 302 and the second through-hole 3011 of the first ring body 301 can be switched between an open position and a closed position as the second ring body 302 is rotated concentrically relative to the first ring body 301. In this embodiment, the detection member is a color-developing sensor.

Figure 17:
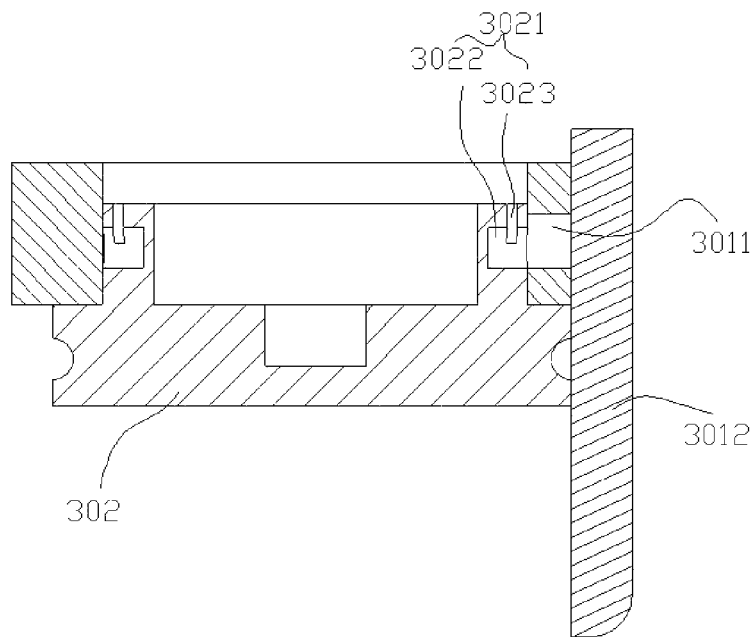
FIG. 17 is a cross-sectional view of the assembled second ring body and first ring body according to Example 3 of the present invention.
Figure 18:
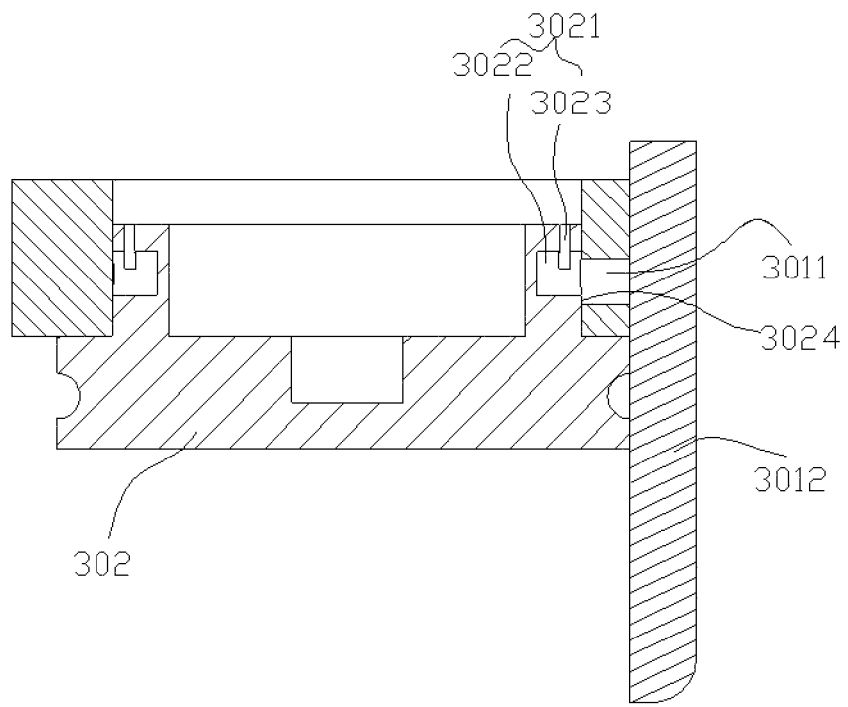
FIG. 18 is a cross-sectional view of the assembled second ring body and first ring body according to Example 3 of the present invention, in which the first ring body is a variation of the first ring body in FIG. 17.

Specifically, as shown in FIG. 17, the liquid channel 3021 comprises slots 3022 which are axially arranged in the annular wall of the second ring body 302 and the third through-holes 3023 which are radially arranged in the annular wall of the second ring body 302. In an open position, liquid flows into the third through-hole 3023 through the slot 3022, then flows into the detection member 3012 for detection. However, in other embodiments, the liquid channel 3021 can be a radial through-hole penetrating through the annular wall of the second ring body 302. For instance, if the third through holes 3023 penetrate through the annular wall of the second ring body 302, then the slots 3022 is unnecessary. In this embodiment, both the axial slots 3022 and the radial third through-holes 3023 are adopted, so that the liquid channel 3021 can be filled with the liquid medicine which would flow into the detection member 3012 in an open position. As a variation of this embodiment, as shown in FIG. 18, in an open position, the opening of the third through-hole 3023 and the opening of the second through-hole 3011 are only in partial communication with each other rather than complete communication, and the lowest point of the second through-hole 3011 is slightly lower than the lowest point of the opening of the third through-hole 3023, so that a height difference 3024 is formed. The height difference 3024 can prevent the liquid flowing into the the second through-hole 3011 from returning to the third through-hole 3023, so as to avoid pollution of the liquid medicine in the infusion bottle or the infusion bag.

Preferably, the annular wall of the second ring body 302 has multiple liquid channels. Namely, multiple axial slots and multiple radial third through-holes corresponding to the respective slots are arranged in the annular wall of the second ring body 302. Correspondingly, multiple detection members 3012 are arranged on the outer surface of the first ring body 301. As the second ring body 302 is rotated concentrically relative to the first ring body 301, the third through holes 3023 of the second ring body 302 are sequentially aligned with the second through holes 3011 of the first ring body 301, so that liquid flows into the detection members 3012 sequentially.

Figure 19:
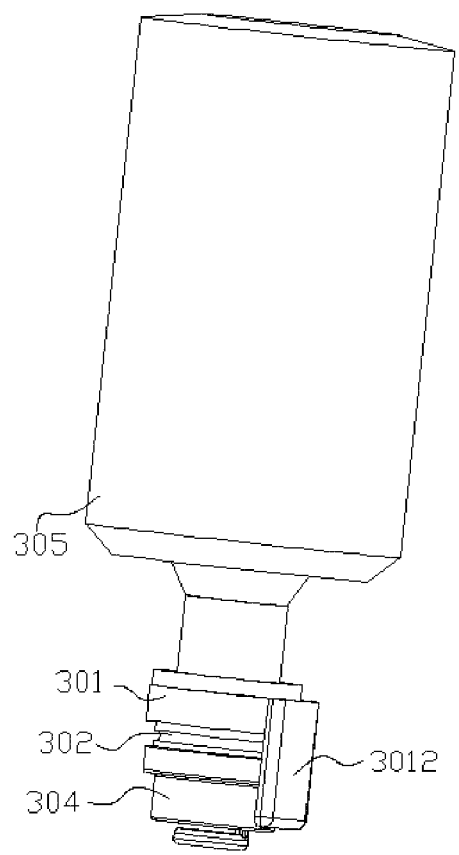
FIG. 19 is a schematic diagram of an infusion accessory according to Example 3 of the present invention being assembled with an infusion bottle.
Figure 20:
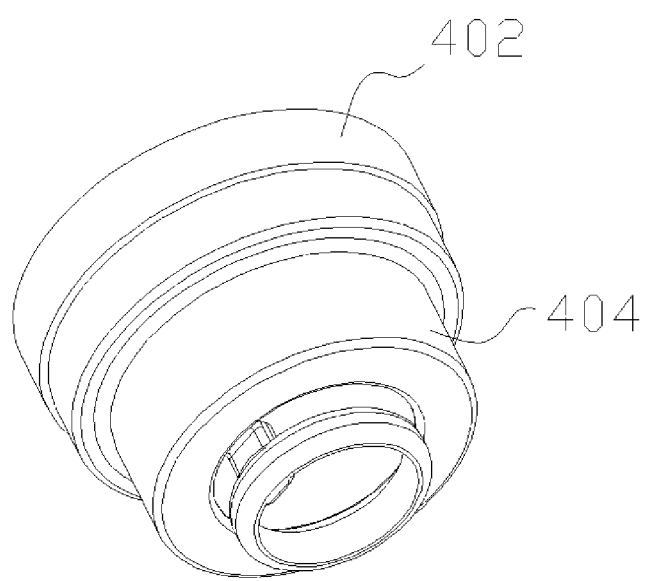
FIG. 20 is a stereo view of an infusion accessory according to Example 4 of the present invention.
Figure 21:
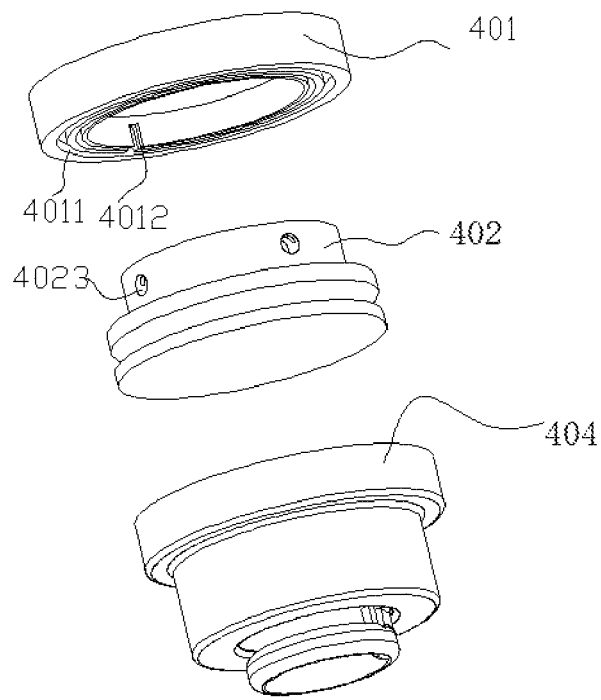
FIG. 21 is an exploded view of an infusion accessory according to Example 4 of the present invention.
Figure 22:
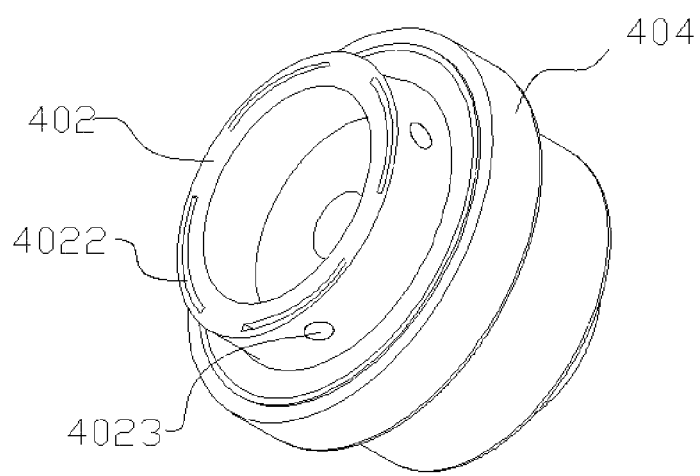
FIG. 22 is a schematic diagram of a first ring body and an outer cover according to Example 4 of the present invention.

FIG. 19 shows the infusion accessory of the present invention assembling with an infusion bottle 305 to form a complete set. An outer cover 304 with a seal assembly for sealing the lid body is sleeved on the lower part of the second ring body 302 and fixedly connected with the second ring body 302. When the outer cover 304 being rotated, the second ring body 302 is driven to rotate concentrically relative to the first ring body 301. The outer cover 304 can be a standard and conventional cap of the existing infusion bottles or infusion bags, so the infusion accessory of the present invention can be integrated with the existing infusion bottles or infusion bags. As a result, the infusion accessory of the present invention is easy to spread the use of it. In addition, the out cover with a seal assembly can isolate the interior of the lid body from the exterior to ensure the interior of the lid body safe, clean and pollution-free.

Example 4

As shown in FIGS. 20-26, in this example, the first portion is a first ring body 401, multiple annular grooves 4011 (for example, in FIG. 23, the first annular groove 40111 and the second annular groove 40112) are arranged between an inner surface and an outer surface of an annular wall of the first ring body 401 in a circumferential direction, and a height of the multiple annular grooves increases progressively from the inner surface to the outer surface with a gradient form, and a notch 4012 is formed in the inner surface of the annular wall of the first ring body, and the detection members are arranged in the annular grooves 40111 and 40112. In this embodiment, the detection members are test papers or detection reagents. The second portion is a second ring body 402 which is rotatable concentrically relative to the first ring body 401, and the first ring body 401 is sleeved on the outer surface of the second ring body 402. The liquid channel 4021 is arranged in the annular wall of the second ring body 402. The liquid channel 4021 of the second ring body 402 and the notch 4012 of the first ring body 401 can be switched between an opening position and a closed position as the second ring body 402 is rotated concentrically relative to the first ring body 401.

Figure 23:
FIG. 23 is a cross-sectional view of a first ring body according to Example 4 of the present invention.
Figure 24:
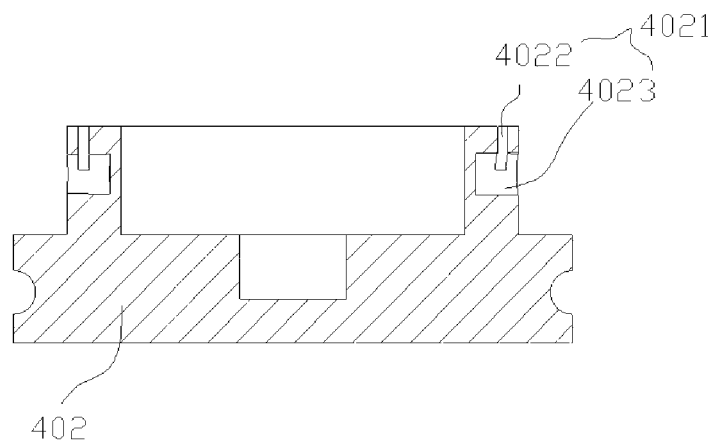
FIG. 24 is a cross-sectional view of a second ring body according to Example 4 of the present invention.
Figure 25:
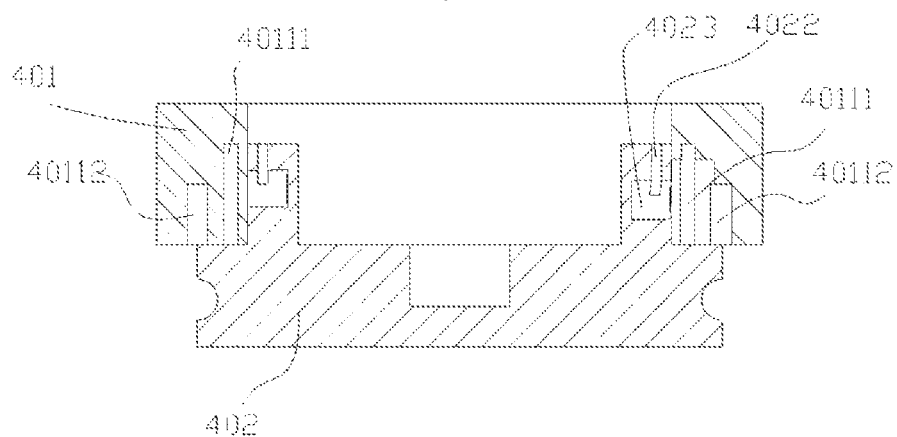
FIG. 25 is a cross-sectional view of the assembled first ring body and second ring body according to Example 4 of the present invention.

Specifically, as shown in FIGS. 23, 24 and 25, the liquid channel 4021 comprises a slot 4022 axially arranged in the annular wall of the second ring body 402 and the fourth through-hole 4023 radially arranged in the annular wall of the second ring body 402. In an opening position, the liquid flows into the fourth through hole 4023 through the slot 4022 and then flows into the notch 4012 of the first ring body 401. In other embodiments, the liquid channel 4021 can also be a radial through-hole penetrating through the annular wall of the second ring body 402. For instance, if the fourth through-hole 4023 penetrates through the annular wall of the second ring body 302, then the slot 4022 is unnecessary. In this embodiment, both the axial slot 4022 and the radial fourth through-hole 4023 are adopted, so that the liquid channel 3021 can be filled with the liquid medicine which would flow into the detection member 3012 in an open position.

Specifically, in this embodiment, multiple axial slots 4022 and multiple fourth through-holes 4023 corresponding to the respective slots are arranged in the annular wall of the second ring body 402, and an opening height of the multiple fourth through-holes 4023 respectively and sequentially corresponds to a height of the annular grooves 4011. In use, as the second ring body 402 is rotated relative to the first ring body 401, one fourth through-hole 4023 located at the lower position is firstly communicated with the notch 4012, and the liquid flows into the annular groove 40111 with the lowest height; as the second ring body 402 continues to be rotated, the communication between the fourth through hole 4023 and the notch is closed; if the second ring body 402 is rotated continuously, another fourth through hole 4023 located at the higher position would communicate with the notch 4012, and the liquid flows into the second annular groove 40112 of which the height is higher than that of the first annular groove 40111. Such operations are repeated to achieve multiple detections.

Figure 26:
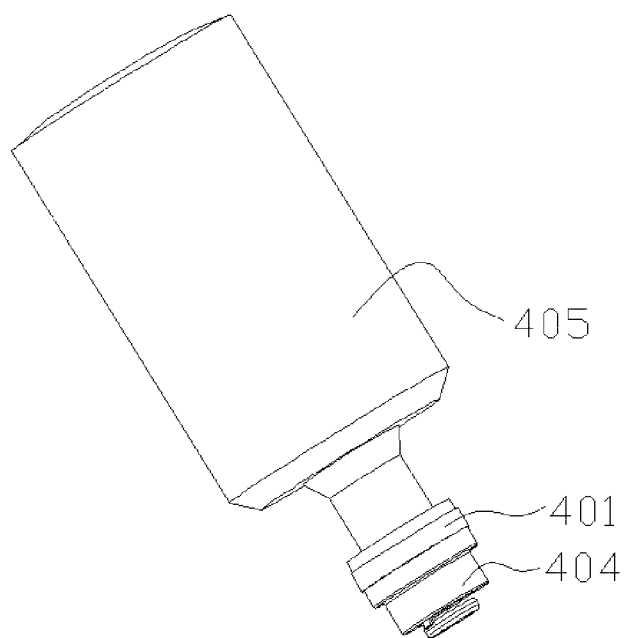
FIG. 26 is a schematic diagram of an infusion accessory according to Example 4 of the present invention being assembled with an infusion bottle.

FIG. 26 shows the infusion accessory of the present invention assembling with an infusion bottle 4305 to form a complete set. An outer cover 404 with a seal assembly for sealing the lid body is sleeved on the second ring body 402 (in FIG. 26, the second ring body 402 is not shown) and fixedly connected with the second ring body 402. When the outer cover 404 being rotated, the second ring body 402 is driven to rotate concentrically relative to the first ring body

401. The outer cover 404 can be a standard and conventional cap of the existing infusion bottles or infusion bags, so the infusion accessory of the present invention can be integrated with the existing infusion bottles or infusion bags. As a result, the infusion accessory of the present invention is easy to spread the use of it. In addition, the out cover with a seal assembly can isolate the interior of the lid body from the exterior to ensure the interior of the lid body safe, clean and pollution-free.

Example 5

Figure 27:
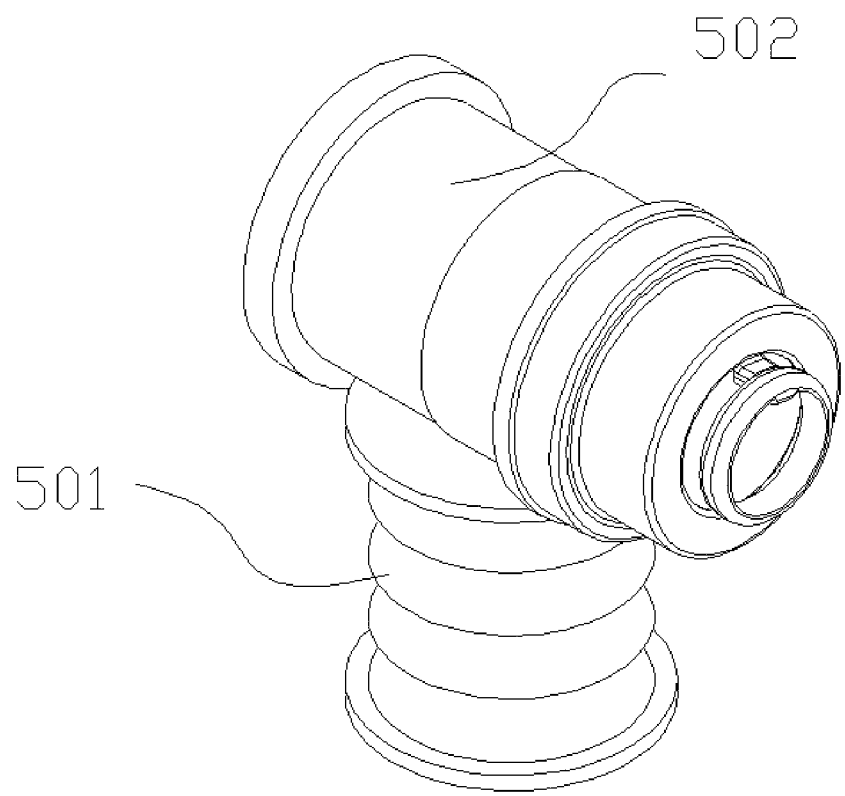
FIG. 27 is a schematic diagram of an infusion accessory according to Example 5 of the present invention.

As shown in FIG. 27, in this embodiment, the infusion accessory is a lid body, comprising a first portion provided with one or more detection members and a second portion having one or more liquid channels. The second portion is a second ring body 502 with the liquid channels arranged in its annular wall. The first portion is a reverse check valve 501 which is connected to the annular wall of the second ring body 502 and is able to extract liquid from the liquid channels of the second ring body 502, and the detection members are arranged in the reverse check valve. When the reverse check valve 501 extracts liquid from the liquid channels, the liquid channels of the second ring body 502 and the detecting members in the reverse check valve 501 are switched in an open position, which enables liquid the liquid channels to flow into the detection members; when the reverse check valve 501 stops extracting liquid from the liquid channels, the liquid channels of the second ring body 502 and the detecting members in the reverse check valve 501 are switched in a close position, so that it is impossible for the liquid in the liquid channels to flow into the detecting members and the liquid that already flows into the detecting members cannot return to the liquid channels.

The invention further provides a method example of detecting infusion liquid parameters by using the infusion accessory of Example 2, comprising the following steps of:

connecting the infusion accessory to an infusion bottle 205, so that the liquid channel 2021 of the second portion of the infusion accessory is in fluid communication with the infusion bottle 205;

changing the relative position between the second portion and the first portion by rotating the first ring body 201, so that the liquid channel 2021 of the second portion is in communication with the first detecting member of the first portion, and liquid in the liquid channel 2021 flows into the detecting member;

changing the relative position between the second portion and the first portion again, so that the communication between the liquid channel and the detection member is closed; and detecting the parameter of the liquid flowing into the detecting member by the first detection member;

adding new liquid medicine into the infusion bottle 204 to adjust the parameter of the liquid in the infusion bottle if the detected parameter of the infusion liquid fails to reach the desired value;

changing the relative position between the second portion and the first portion again after addition of new liquid medicine, so that the liquid channel 2021 of the second portion is in communication with the second detecting member of the first portion, and liquid in the liquid channel flows into the second detecting member;

changing the relative position between the second portion and the first portion again, so that the communication between the liquid channel and the second detection member is closed; and detecting the parameter of the liquid flowing into the second detecting member by the second detection member;

adding new liquid medicine into the infusion bottle 204 to adjust the parameter of the liquid in the infusion bottle if the detected parameter of the infusion liquid still fails to reach the desired value, and repeating the above steps until the parameter of the liquid in the infusion bottle or the infusion bag reaches the desired value.

The invention further provides another method example of detecting infusion liquid parameters by using the infusion accessory of Example 2, comprising the following steps of:

connecting the infusion accessory to an infusion bottle 205, so that the liquid channel of the second portion of the infusion accessory is in fluid communication with liquid in the infusion bottle 205;

changing the relative position between the second portion and the first portion by rotating the first portion, so that the liquid channel 2021 of the second portion is in communication with the first detecting member of the first portion, and liquid in the liquid channel flows into the first detecting member;

changing the relative position between the second portion and the first portion again, so that the communication between the liquid channel 2021 and the first detection member is closed; and detecting the first parameter (such as the osmotic pressure) of the liquid flowing into the first detecting member by the first detection member;

changing the relative position between the second portion and the first portion again by rotating the first portion, so that the liquid channel 2021 of the second portion is in communication with the second detecting member of the first portion, and liquid in the liquid channel flows into the second detecting member;

changing relative position between the second portion and the first portion again by rotating the first portion, so that the communication between the liquid channel and the second detection member is closed; and detecting the second parameter (such as the electrolysis degree) of the liquid flowing into the second detecting member by the second detection member; repeating the above steps until all desired parameters of the liquid are detected.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

What is claimed is:

1. An infusion accessory capable of detecting infusion liquid parameters, which is a lid body, comprising:
   a first portion provided with one or more detecting members and a second portion having one or more liquid channels;
   wherein relative position changes occur between the first portion and the second portion when an external force is applied, the liquid channels of the second portion and the detecting members of the first portion are switched between an open position and a closed position as position changes occur between the first portion and the second portion, the open position enables communication between the liquid channels and the detecting members so that liquid in the liquid channels flows into the detecting members, and the closed position enables sealing between the liquid channels and the detecting members so that it is impossible for the liquid in the liquid channels to flow into the detecting members and the liquid that already flows into the detecting members cannot return to the liquid channels.

2. The infusion accessory capable of detecting infusion liquid parameters according to claim 1,
wherein the first portion is a first ring body, one or more containing chambers are arranged in an annular wall of the first ring body, and the detection members are arranged in the containing chambers of the annular wall of the first ring body;
the second portion is a second ring body which is rotatable concentrically relative to the first ring body, and the liquid channels are arranged in an annular wall of the second ring body;
the liquid channels of the second ring body and the containing chambers of the first ring body are switched between an open position and a closed position as the second ring body is rotated concentrically relative to the first ring body.

3. The infusion accessory capable of detecting infusion liquid parameters according to claim 2,
wherein the second ring body is disposed above the first ring body, and the one or more containing chambers of the first ring body are slots or cavities axially arranged in the annular wall of the first ring body, and the liquid channels of the second ring body are arranged to be vertical or inclined channels.

4. The infusion accessory capable of detecting infusion liquid parameters according to claim 3, wherein multiple slots or cavities are axially arranged in a circumference direction of the annular wall of the first ring body, and the liquid channels and the multiple slots or cavities are sequentially switched between an open position and a closed position as the second ring body is rotated concentrically relative to the first ring body.

5. The infusion accessory capable of detecting infusion liquid parameters according to claim 1, wherein the first portion is a first ring body, one or more containing chambers are arranged in an annular wall of the first ring body, and the detection members are arranged in the containing chambers of the annular wall of the first ring body;
the second portion is a second ring body, and the liquid channels are arranged in an annular wall of the second ring body;
the first ring body is rotatable concentrically relative to the second ring body, and the liquid channels of the second ring body and the containing chambers of the first ring body are switched between an open position and a closed position as the first ring body is rotated concentrically relative to the second ring body.

6. The infusion accessory capable of detecting infusion liquid parameters according to claim 5, wherein the second ring body is sleeved on the first ring body, and each containing chamber comprises a slot or cavity axially arranged in the annular wall of the first ring body and a first through-hole radially arranged in the annular wall of the first ring body, and the liquid channels are arranged on an inner surface of the annular wall of the second ring body.

7. The infusion accessory capable of detecting infusion liquid parameters according to claim 6, wherein multiple slots and multiple first through-holes corresponding to the respective slots are arranged in the annular wall of the first ring body, the liquid channels and the multiple first through-holes are sequentially switched between an open position and a closed position as the first ring body is rotated concentrically relative to the second ring body.

8. The infusion accessory capable of detecting infusion liquid parameters according to claim 5, when the liquid channels of the second ring body and the containing chambers of the first ring body are switched in an open position, a backflow prevention structure is formed between an opening of the liquid channels and an opening of the containing chambers, so as to prevent the liquid that already flows into the containing chambers from returning to the liquid channels.

9. The infusion accessory capable of detecting infusion liquid parameters according to claim 1, wherein the first portion is a first ring body, and one or more detection members are arranged on an outer surface of the first ring body, one or more second through-holes communicated with the one or more detection members are formed in an annular wall of the first ring body;
the second portion is a second ring body which is rotatable concentrically relative to the first ring body, and the liquid channels are arranged in an annular wall of the second ring body;
the first ring body is sleeved on an outer surface the second ring body, the liquid channels of the second ring body and the second through-holes of the first ring body are switched between an open position and a closed position as the second ring body is rotated concentrically relative to the first ring body.

10. The infusion accessory capable of detecting infusion liquid parameters according to claim 9, wherein the liquid channels comprise slots axially arranged in the annular wall of the second ring body and third through-holes radially arranged in the annular wall of the second ring body.

11. The infusion accessory capable of detecting infusion liquid parameters according to claim 9, wherein the liquid channels are through-holes radially arranged in the annular wall of the second ring body.

12. The infusion accessory capable of detecting infusion liquid parameters according to claim 1, wherein the first portion is a first ring body, multiple annular grooves are arranged between an inner surface and an outer surface of an annular wall of the first ring body in a circumferential direction, and a height of the multiple annular grooves increases progressively from the inner surface to the outer surface with a gradient form, and notches are formed in the inner surface of the annular wall of the first ring body, and the detection members are arranged in the annular grooves;
the second portion is a second ring body which is rotatable concentrically relative to the first ring body, and the first ring body is sleeved on an outer surface of the second ring body, and the liquid channels are arranged in an annular wall of the second ring body;
the liquid channels of the second ring body and the notches of the first ring body are switched between an open position and a closed position as the second ring body is rotated concentrically relative to the first ring body.

13. The infusion accessory capable of detecting infusion liquid parameters according to claim 12, wherein the liquid channels comprise slots axially arranged in the annular wall of the second ring body and fourth through-holes radially arranged in the annular wall of the second ring body.

14. The infusion accessory capable of detecting infusion liquid parameters according to claim 13, wherein multiple slots and multiple fourth through-holes corresponding to the respective slots are arranged in the annular wall of the second ring body, and an opening height of the multiple fourth through-holes respectively and sequentially corresponds to a height of the annular grooves.

15. The infusion accessory capable of detecting infusion liquid parameters according to claim 12, wherein the liquid channels are through-holes radially arranged in the annular wall of the second ring body.

16. The infusion accessory capable of detecting infusion liquid parameters according to claim 1, wherein the infusion liquid parameters comprise a pH value, an electrolysis degree, an osmotic pressure, a concentration of effective components, and/or insoluble particles.

17. The infusion accessory capable of detecting infusion liquid parameters according to claim 16, wherein the first portion is provided with multiple detection members, and the multiple detection members are used to detect the same infusion liquid parameter or different infusion liquid parameters respectively.

18. An infusion accessory capable of detecting infusion liquid parameters, which is a lid body, comprising:
    a first portion provided with one or more detecting members and a second portion having one or more liquid channels;
    the second portion is a second ring body, and the liquid channels are arranged in an annular wall of the second ring body;
    the first portion is a reverse check valve which is connected to the annular wall of the second ring body and is able to extract liquid from the liquid channels of the second ring body, and the detection members are arranged in the reverse check valve;
    when the reverse check valve extracts liquid from the liquid channels, the liquid channels of the second ring body and the detecting members in the reverse check valve are switched in an open position, which enables liquid the liquid channels to flow into the detection members; when the reverse check valve stops extracting liquid from the liquid channels, the liquid channels of the second ring body and the detecting members in the reverse check valve are switched in a closed position, so that it is impossible for the liquid in the liquid channels to flow into the detecting members and the liquid that already flows into the detecting members cannot return to the liquid channels.

19. A method of detecting infusion liquid parameters by using an infusion accessory, which is a lid body and is able to be connected to an infusion bottle or an infusion bag, comprising an outer cover with a seal assembly for sealing the lid body, and a first portion provided with one detecting member and a second portion having one liquid channel;
    wherein relative position changes occur between the first portion and the second portion when an external force is applied, the liquid channel of the second portion and the detecting member of the first portion are switched between an open position and a closed position as position changes occur between the first portion and the second portion, the open position enables communication between the liquid channel and the detecting member so that liquid in the liquid channel flows into the detecting member, and the closed position enables sealing between the liquid channel and the detecting member so that it is impossible for the liquid in the liquid channel to flow into the detecting member and the liquid that already flows into the detecting member cannot return to the liquid channel;
    the method comprising the following steps of:
    connecting the infusion accessory to an infusion bottle or an infusion bag, so that the liquid channel of the second portion of the infusion accessory is in fluid communication with liquid in the infusion bottle or the infusion bag;
    changing relative position between the second portion and the first portion, so that the liquid channel of the second portion is in communication with the detecting member of the first portion, and liquid in the liquid channel flows into the detecting member;
    changing relative position between the second portion and the first portion again, so that the communication between the liquid channel and the detection member is closed;
    detecting the parameter of the liquid flowing into the detecting member by the detection member.

20. A method of detecting infusion liquid parameters by using an infusion accessory, which is a lid body and is able to be connected to an infusion bottle or an infusion bag, comprising an outer cover with a seal assembly for sealing the lid body, and a first portion provided with multiple detecting members and a second portion having one liquid channel, wherein the multiple detecting members are used to detect the same parameter;
    wherein relative position changes occur between the first portion and the second portion when an external force is applied, the liquid channel of the second portion and the detecting members of the first portion are switched between an open position and a closed position as position changes occur between the first portion and the second portion, the open position enables communication between the liquid channel and one of the detecting members so that liquid in the liquid channel flows into the detecting member, and the closed position enables sealing between the liquid channel and the detecting members so that it is impossible for the liquid in the liquid channel to flow into the detecting members and the liquid that already flows into the detecting members cannot return to the liquid channel;
    the method comprising the following steps of:
    connecting the infusion accessory to an infusion bottle or an infusion bag, so that the liquid channel of the second portion of the infusion accessory is in fluid communication with liquid in the infusion bottle or the infusion bag;
    changing relative position between the second portion and the first portion, so that the liquid channel of the second portion is in communication with a first detecting member of the first portion, and liquid in the liquid channel flows into the first detecting member;
    changing relative position between the second portion and the first portion again, so that the communication between the liquid channel and the first detection member is closed;
    detecting the parameter of the liquid flowing into the first detecting member by the first detection member;
    adding new liquid medicine into the infusion bottle or the infusion bag to adjust the parameter of the liquid in the infusion bottle or the infusion bag if the detected parameter of the infusion liquid fails to reach the desired value;
    changing relative position between the second portion and the first portion again after addition of new liquid medicine, so that the liquid channel of the second portion is in communication with a second detecting member of the first portion, and liquid in the liquid channel flows into the second detecting member;

changing relative position between the second portion and the first portion again, so that the communication between the liquid channel and thesecond detection member is closed;

detecting the parameter of the liquid flowing into the second detecting member by the second detection member;

adding new liquid medicine into the infusion bottle or the infusion bag to adjust the parameter of the liquid in the infusion bottle or the infusion bag if the detected parameter of the infusion liquid still fails to reach the desired value, and repeating the above steps until the parameter of the liquid in the infusion bottle or the infusion bag reaches the desired value.

21. A method of detecting infusion liquid parameters by using an infusion accessory, which is a lid body and is able to be connected to an infusion bottle or an infusion bag, comprising an outer cover with a seal assembly for sealing the lid body, and a first portion provided with multiple detecting members and a second portion having one liquid channel, wherein the multiple detecting members are different and are used to detect different parameters;

wherein relative position changes occur between the first portion and the second portion when an external force is applied, the liquid channel of the second portion and the detecting members of the first portion are switched between an open position and a closed position as position changes occur between the first portion and the second portion, the open position enables communication between the liquid channel and one of the detecting members so that liquid in the liquid channel flows into the detecting member, and the closed position enables sealing between the liquid channel and the detecting members so that it is impossible for the liquid in the liquid channel to flow into the detecting members and the liquid that already flows into the detecting members cannot return to the liquid channel;

the method comprising the following steps of:

connecting the infusion accessory to an infusion bottle or an infusion bag, so that the liquid channel of the second portion of the infusion accessory is in fluid communication with liquid in the infusion bottle or the infusion bag;

changing relative position between the second portion and the first portion, so that the liquid channel of the second portion is in communication with a first detecting member of the first portion, and liquid in the liquid channel flows into the first detecting member;

changing relative position between the second portion and the first portion again, so that the communication between the liquid channel and the first detection member is closed;

detecting a first parameter of the liquid flowing into the first detecting member by the first detection member;

changing relative position between the second portion and the first portion again, so that the liquid channel of the second portion is in communication with a second detecting member of the first portion, and liquid in the liquid channel flows into the second detecting member;

changing relative position between the second portion and the first portion again, so that the communication between the liquid channel and the second detection member is closed;

detecting a second parameter of the liquid flowing into the second detecting member by the second detection member;

repeating the above steps until all desired parameters of the liquid are detected.

\* \* \* \* \*